(12) United States Patent
Heneghan et al.

(10) Patent No.: US 10,154,790 B2
(45) Date of Patent: Dec. 18, 2018

(54) METHOD AND SYSTEM FOR MONITORING SLEEP

(75) Inventors: Conor Heneghan, Dublin (IE); Eric C.-P. Chua, Dublin (IE); Gareth McDarby, Wicklow (IE)

(73) Assignee: University College Dublin, National University of Ireland (IE)

( * ) Notice: Subject to any disclaimer, the term of this patent is extended or adjusted under 35 U.S.C. 154(b) by 694 days.

(21) Appl. No.: 12/674,344

(22) PCT Filed: Aug. 11, 2008

(86) PCT No.: PCT/EP2008/006599
§ 371 (c)(1),
(2), (4) Date: Feb. 19, 2010

(87) PCT Pub. No.: WO2009/024273
PCT Pub. Date: Feb. 26, 2009

(65) Prior Publication Data
US 2011/0124979 A1  May 26, 2011

(30) Foreign Application Priority Data

Aug. 21, 2007 (IE) .................................. S2007/0595

(51) Int. Cl.
*A61B 5/00* (2006.01)
*A61B 5/024* (2006.01)
*A61B 5/04* (2006.01)

(52) U.S. Cl.
CPC .......... *A61B 5/024* (2013.01); *A61B 5/02405* (2013.01); *A61B 5/04012* (2013.01); *A61B 5/4812* (2013.01); *A61B 5/4818* (2013.01)

(58) Field of Classification Search
CPC ....... A61B 5/024; A61B 5/021; A61B 5/0205; A61B 5/02416
See application file for complete search history.

(56) References Cited

U.S. PATENT DOCUMENTS

| | | | |
|---|---|---|---|
| 5,105,354 A | 4/1992 | Nishimura | |
| 5,280,791 A | 1/1994 | Lavie | |
| 5,588,425 A * | 12/1996 | Sackner et al. | 600/523 |

(Continued)

FOREIGN PATENT DOCUMENTS

| | | | |
|---|---|---|---|
| CN | 1613425 A * | 5/2005 | |
| FR | 2859094 A | 3/2005 | |

(Continued)

OTHER PUBLICATIONS

English translation of CN1613425A.*

(Continued)

*Primary Examiner* — John R Downey
*Assistant Examiner* — Shirley Jian
(74) *Attorney, Agent, or Firm* — Botos Churchill IP Law LLP

(57) ABSTRACT

A method of monitoring sleep comprises simultaneously recording a person's electrocardiogram (ECG) and photoplethysmogram (PPG), deriving a plurality of parameters from the recorded data, and providing an output indicative of a sleep characteristic based upon an analysis of the parameters. The ECG and PPG may be recorded using an apparatus which is a combination of a Holter monitor and a pulse oximeter, which is wearable in ambulatory manner.

27 Claims, 8 Drawing Sheets

(56) References Cited

U.S. PATENT DOCUMENTS

| | | | |
|---|---|---|---|
| 5,769,084 A | 6/1998 | Katz et al. | |
| 5,902,250 A * | 5/1999 | Verrier et al. | 600/515 |
| 6,117,075 A * | 9/2000 | Barnea | 600/300 |
| 7,024,234 B2 * | 4/2006 | Margulies et al. | 600/324 |
| 7,027,621 B1 * | 4/2006 | Prokoski | G06K 9/00255 |
| | | | 180/272 |
| 7,059,275 B2 * | 6/2006 | Laitinen | A01K 11/008 |
| | | | 119/720 |
| 7,248,915 B2 * | 7/2007 | Ronnholm | 600/544 |
| 7,367,949 B2 * | 5/2008 | Korhonen | A61B 5/1106 |
| | | | 600/481 |
| 7,578,793 B2 * | 8/2009 | Todros et al. | 600/484 |
| 7,674,230 B2 * | 3/2010 | Reisfeld | 600/484 |
| 7,794,406 B2 * | 9/2010 | Reisfeld et al. | 600/500 |
| 7,803,118 B2 * | 9/2010 | Reisfeld et al. | 600/483 |
| 7,803,119 B2 * | 9/2010 | Reisfeld | 600/483 |
| 7,827,010 B2 * | 11/2010 | Szasz | G01R 29/26 |
| | | | 702/189 |
| 2002/0169384 A1 | 11/2002 | Kowallik et al. | |
| 2004/0015091 A1 * | 1/2004 | Greenwald | A61B 5/02125 |
| | | | 600/513 |
| 2004/0059236 A1 * | 3/2004 | Margulies et al. | 600/500 |
| 2005/0010116 A1 * | 1/2005 | Korhonen | A61B 5/1106 |
| | | | 600/481 |
| 2005/0148895 A1 | 7/2005 | Misczynski et al. | |
| 2005/0190065 A1 * | 9/2005 | Ronnholm | 340/575 |
| 2006/0041201 A1 | 2/2006 | Behbehani et al. | |
| 2006/0142968 A1 * | 6/2006 | Han et al. | 702/120 |
| 2006/0224073 A1 | 10/2006 | Lin et al. | |
| 2006/0241708 A1 | 10/2006 | Boute | |
| 2007/0060874 A1 * | 3/2007 | Nesbitt | A61M 5/14228 |
| | | | 604/80 |
| 2007/0173728 A1 * | 7/2007 | Pu et al. | 600/484 |
| 2007/0213620 A1 * | 9/2007 | Reisfeld | 600/484 |
| 2007/0213621 A1 * | 9/2007 | Reisfeld et al. | 600/484 |
| 2007/0213622 A1 * | 9/2007 | Reisfeld | 600/484 |
| 2007/0213624 A1 * | 9/2007 | Reisfeld et al. | 600/504 |
| 2008/0269583 A1 * | 10/2008 | Reisfeld | 600/364 |
| 2011/0124979 A1 * | 5/2011 | Heneghan et al. | 600/301 |

FOREIGN PATENT DOCUMENTS

| | | |
|---|---|---|
| WO | 2005067790 A | 7/2005 |
| WO | WO 2008132736 A2 * | 11/2008 |

OTHER PUBLICATIONS

International Search Report for PCT International Patent Application No. PCT/EP2008/006599, dated Nov. 24, 2008.

Pagani et al., Detection of Central and Obstructive Sleep Apnea in Children Using Pulse Transmit Time, Computers in Cardiology 2002, Sep. 22, 2002, pp. 529-532, vol. 29, New York, NY.

Guilleminault et al., "Variability of respiratory effort in relation to sleep stages in normal controls and upper airway resistance syndrome patients", Sleep Medicine 2 (2001) 397-406.

Hodsman et al, "Data collection and analysis from a respiratory inductance plethysmograph", International Journal of Clinical Monitoring and Computing 4:237-241, 1987.

Pagani et al., "Power Spectral Analysis of Heart Rate and Arterial Pressure Variabilities as a Marker of Sympatho—Vagal Interaction in Man and Conscious Dog", http://circres.ahajournals.org/byguest, Dec. 22, 2017.

* cited by examiner

Example of DFA for n = 100.

Solid line: y[k], demeaned and integrated RR intervals.
Dotted line: $y_n[k]$, piece-wise least squares fit of y[k].

METHOD AND SYSTEM FOR MONITORING SLEEP

CROSS REFERENCE TO RELATED APPLICATIONS

The present application is a national phase entry under 35 U.S.C. § 371 of International Application No. PCT/EP2008/006599, filed Aug. 11, 2008, now Publication No. WO/2009/024273, published on Feb. 26, 2009, published in English, which claims priority from Irish Patent Application No. S2007/0595, filed Aug. 21, 2007, all of which are incorporated herein by reference.

FIELD OF THE INVENTION

The present invention relates to the monitoring of sleep, including sleep state or sleepiness levels of humans in a convenient way, and more specifically to a method and system for acquiring and processing the related information.

BACKGROUND

Monitoring of sleep state and sleepiness is useful in a clinical context for assessing subjects with suspected obstructive sleep apnoea, and in an industrial context for monitoring sleepiness in vehicle drivers and in actual work environments, particularly where sleepiness-related accidents can have serious consequences.

Obstructive sleep apnoea syndrome (OSAS) is a prevalent but under-diagnosed condition with serious cardiovascular consequences, and is highly treatable. Standard in-laboratory testing for OSAS involves an overnight study to assess severity of apnoea and sleep fragmentation, and may also involve an all-day study to assess daytime sleepiness. Assessment of sleep fragmentation can be achieved by analysing the overnight study to produce a chart of sleep stages, and the assessment of daytime sleepiness can be accomplished by measuring on multiple occasions over a day, the time taken for subjects to fall asleep (the so-called Multiple Sleep Latency Test).

However, due to increasing public awareness of OSAS and resource constraints in healthcare systems, in-laboratory testing for OSAS suffers from low availability in many countries. Therefore there is considerable interest among the professional societies in sleep medicine in the development of reliable low-cost techniques suitable for use in the home environment for identification of subjects with OSAS.

In the general population, the problem of sleepiness is recognised as a contributing factor to occupational and vehicular accidents. In the area of transportation safety, there is a lot of interest in methods to monitor driver fatigue. At the same time, there is interest in techniques that can complement existing in-laboratory clinical tools by assessing sleepiness over prolonged periods in the actual work environment.

A variety of techniques have been disclosed in the background art for addressing the need for sleep state and sleepiness monitoring outside of the laboratory environment.

For sleep state monitoring, portable systems incorporating the required signals for standard in-laboratory monitoring (2 channels of electro-encephalography, 2 channels of electro-oculography and 1 channel of electro-myography) have been developed. However, these systems require substantial clinical support to operate in the home environment. Subjects usually have to visit the sleep clinic before and after the overnight study to have the equipment set-up and removed. They also require the attachment of electrodes to the head, which can be disruptive and inconvenient.

Another method is to use a subset of the standard signals (such as a single EEG channel) to obtain an approximation. However, EEG monitoring at home requires significant user expertise, and it does not allow concurrent apnoea detection. Methods using other signals to provide estimates have also been proposed. These methods include actimetry, ECG plus respiration, and peripheral arterial tone plus actimetry. However, actimetry alone can only distinguish between wake and sleep but not the different stages of sleep, and also does not allow concurrent apnoea detection. Peripheral arterial tone monitoring requires proprietary and costly hardware and associated software. Respiration monitoring may be prone to sensor displacement in a home environment.

For sleepiness monitoring outside laboratory conditions, methods using eyelid closures, head movements, video surveillance, EEG, and actimetry have been proposed. However, methods using eyelid closures, head movements, video surveillance are not portable, so while it is feasible for applications such as driver sleepiness monitoring, it is not suitable for applications requiring ambulatory monitoring. EEG is ambulatory, but technical difficulties for long-term monitoring exist, and again it is inconvenient to have electrodes attached to the scalp. Sleepiness can be more objectively assessed with measurements such as the Psychomotor Vigilance Test (PVT) which measures a subject's reaction times. It has been shown that in a given subject, the reaction times will decrease as the person becomes sleepier—therefore PVT scores are used as a surrogate for sleepiness. However, PVT scoring takes approximately 10 minutes to carry out, and requires the subject's active attention so cannot be used for in-task monitoring of sleepiness.

SUMMARY

In its broadest aspect the present invention provides a method of monitoring sleep, comprising recording a person's electrocardiogram (ECG), deriving a parameter from the recorded data, and providing an output indicative of a sleep characteristic based upon an analysis of the parameter.

In preferred embodiments the present invention provides a method of monitoring sleep, comprising simultaneously recording a person's electrocardiogram (ECG) and photoplethysmogram (PPG), deriving a plurality of parameters from the recorded data, and providing an output indicative of a sleep characteristic based upon an analysis of the parameters.

Preferably the ECG and PPG are recorded using a recording apparatus wearable in ambulatory manner, most preferably a combination of a Holter monitor and a pulse oximeter.

In a preferred embodiment the parameters include RR interval, pulse amplitude, pulse arrival time and respiratory rate.

In one embodiment the sleep characteristic is sleepiness; in another it is the state of sleep.

The invention also provides a system for monitoring sleep, comprising an apparatus for simultaneously recording a subject's electrocardiogram (ECG) and photoplethysmogram (PPG), and a data processor for deriving a plurality of parameters from the recorded data and providing an output indicative of a sleep characteristic based upon an analysis of the parameters.

The invention enables the monitoring of sleep state or sleepiness level of human subjects in a convenient, non-invasive and low-cost fashion. In particular, the present invention provides the advantage that it requires a minimal number of signals (two signals) that are robust in the home environment to perform sleep state monitoring, and these signals can also be used concurrently for apnoea detection, which is another significant aspect of sleep apnoea diagnostics. In addition, these signals can be acquired in a non-invasive and fully ambulatory manner using relatively low-cost hardware.

The invention has applications to clinical assessment of subjects with suspected sleep apnoea or sleep disorders that disrupt sleep state patterns, such as narcolepsy, monitoring of sleep and sleepiness patterns in healthy subjects, fitness-for-duty tests for sleepiness, sleepiness monitoring in actual work environments such as machinery operation, and driver sleepiness monitoring.

BRIEF DESCRIPTION OF THE DRAWINGS

Embodiments of the present invention will now be described, by way of example, with reference to the accompanying drawings in which.

DETAILED DESCRIPTION

Figure 1:
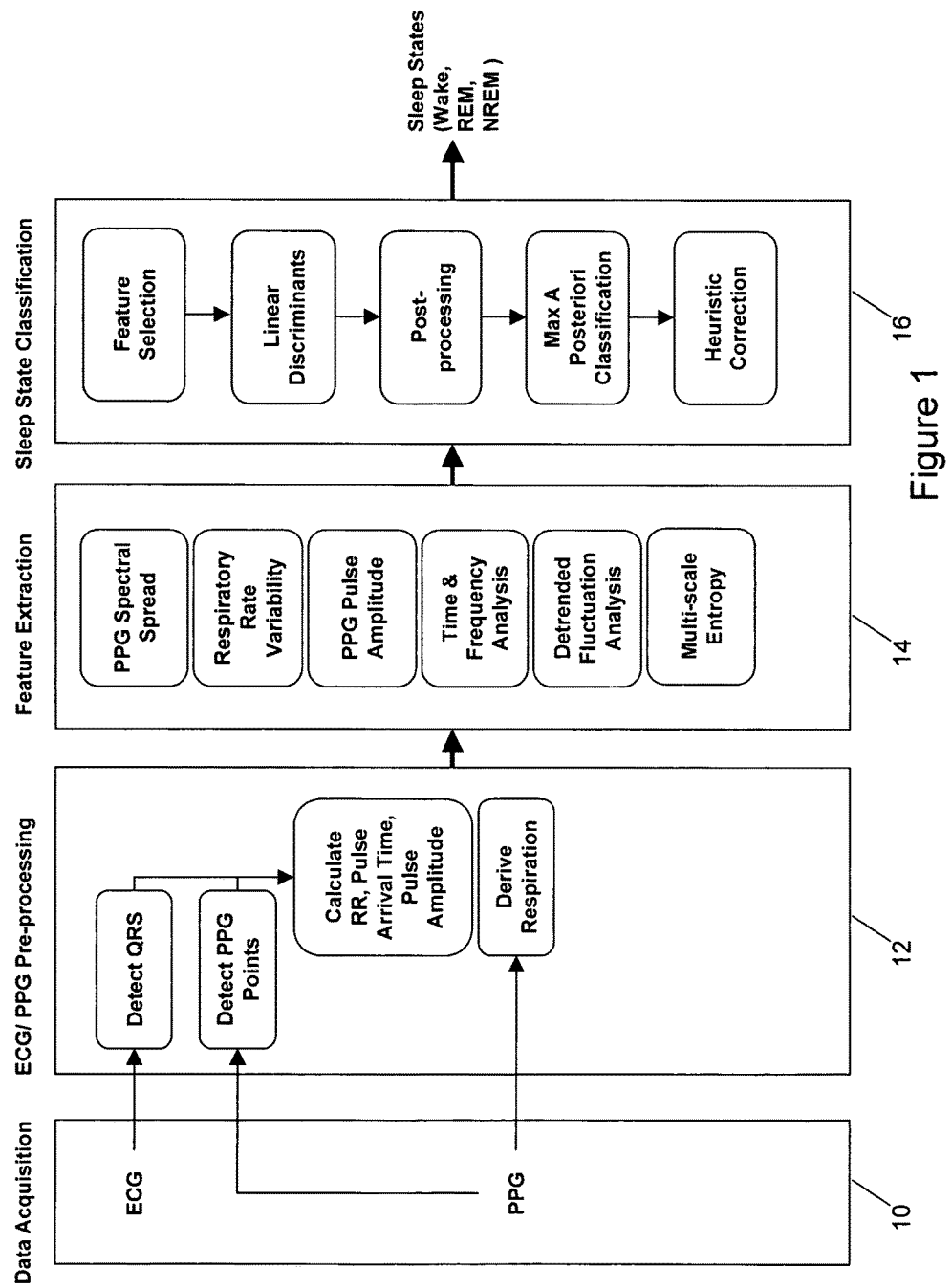
FIG. 1 is a block schematic diagram of a system for estimating sleep states according to a first embodiment of the present invention.

FIG. 1 is a block schematic diagram of a system for estimating sleep states according to a first embodiment of the present invention. The system comprises a data acquisition apparatus 10 and data processing stages 12, 14 and 16.

The data acquisition apparatus 10 is a combined Holter monitor and pulse oximeter. The Holter monitor is capable of recording three data channels. In this embodiment two of the channels are used to record two ECG waveforms, and the remaining channel to record the PPG waveform.

In particular, two channels of ECG (modified lead V5 and modified lead V1) and one channel of finger PPG (index finger of non-dominant hand) are recorded simultaneously. Only one channel of ECG (modified lead V5) out of the two channels recorded is used for this embodiment, the other being recorded to provide redundancy and to allow for the possibility of calculating an ECG-derived respiration signal. The data is stored in flash memory within a portable storage device carried by the subject in a sling pouch or in a pocket, and is transferred offline to the data processing stages 12 to 16 for further analysis. The data processing stages 12 to 16 can be implemented by a suitably programmed computer. Alternatively, the portable device can have processing capability so that real-time monitoring can be performed.

It will be noted that this arrangement avoids the subject having to be connected to a bulky recording system. This is in contrast to the current technique of monitoring sleep in a hospital which requires multiple cables to be attached to the subject, these cables terminating at the other end in a bulky recording system. In that arrangement the subject is 'tied' to the recording system for the entire night, as to even go to the washroom would require a technician to remove and subsequently reattach all the cables. In the present embodiment the subject is fully ambulatory.

In the pre-processing stage 12, various parameters are derived from the ECG and PPG. In the feature extraction stage 14, various features suitable for classifying sleep states are extracted from the various parameters derived in stage 12. Finally, in the classification stage 16, a subset of features is fed into a classifier model to obtain estimated sleep states.

Figure 2:
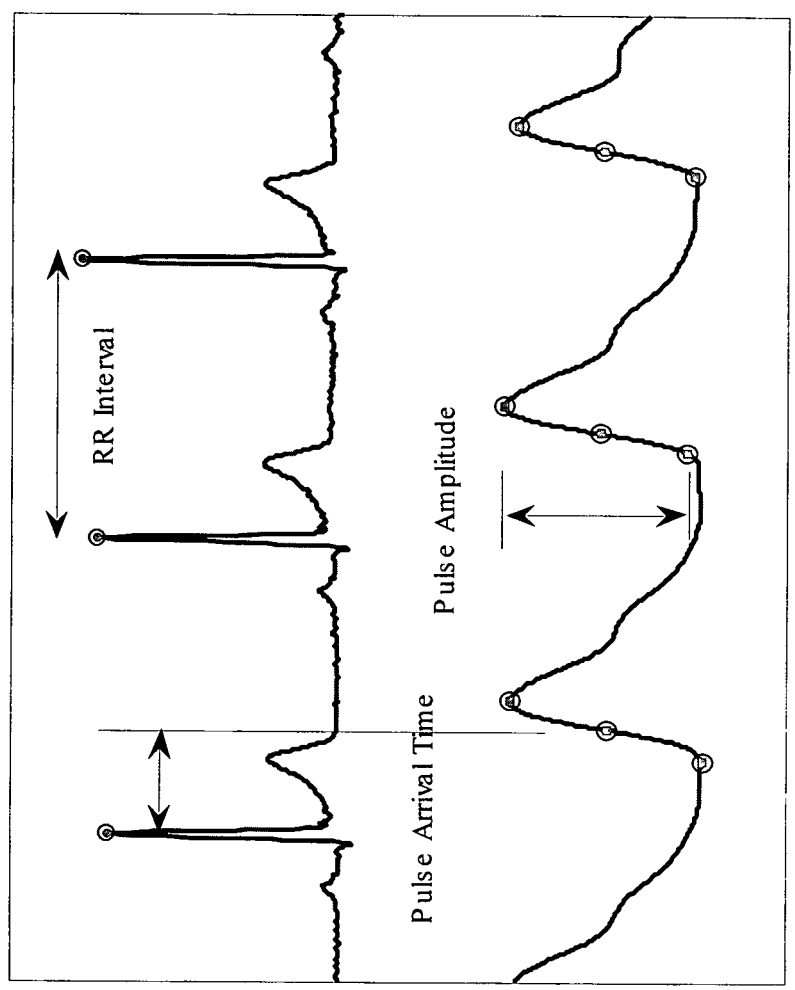
FIG. 2 are waveform diagrams showing parameters derived from the ECG (upper waveform) and PPG (lower waveform) which are used in the first embodiment (as well as the other embodiments).

FIG. 2 are waveform diagrams showing parameters derived in the pre-processing stage 12 from the ECG (upper waveform) and PPG (lower waveform). Four parameters, namely RR interval, pulse amplitude, pulse arrival time and respiration are derived from the ECG and PPG signals. The first three are defined based on characteristic points on the waveforms, shown as small circles in FIG. 2. RR intervals are the time differences between successive QRS peaks, which can be detected using conventional methods such as Hilbert-transformation with thresholding. To derive pulse amplitude, the PPG is high-pass filtered at 0.05 Hz to remove a very low frequency baseline and then normalised to unit median pulse amplitude as raw PPG values varies considerably between subjects depending on physiological factors such as body position and technical factors such as probe application pressure. Pulse amplitude is then calculated as the beat by beat trough to peak amplitude, and peaks and troughs can be detected using conventional methods such as derivative with thresholding. Pulse arrival time is calculated as the time interval between the R peak on the ECG and the point with maximum gradient on the systolic edge of the PPG. Respiration is obtained by band-pass filtering the PPG between 0.06 and 0.5 Hz.

In the feature extraction stage 14 the following features are calculated:

(a) PPG spectral spread. This is the Shannon entropy of the power spectral density of the PPG signal, calculated for consecutive thirty-second epochs. This feature is useful for identifying movement associated with wakefulness as the power spectral density of PPG waveforms when subjects are not moving are characterised by a concentration of spectral power around the heart rate and its first few higher harmonics. In contrast, spectral power is more evenly spread out for waveforms contaminated by artefact.

(b) PPG pulse amplitude. This is the mean of the pulse amplitude, calculated for ten-minute epochs sliding at thirty-second intervals. This feature is useful for identifying peripheral vasoconstriction associated with REM sleep, which causes a decrease in pulse amplitude.

Figure 7:
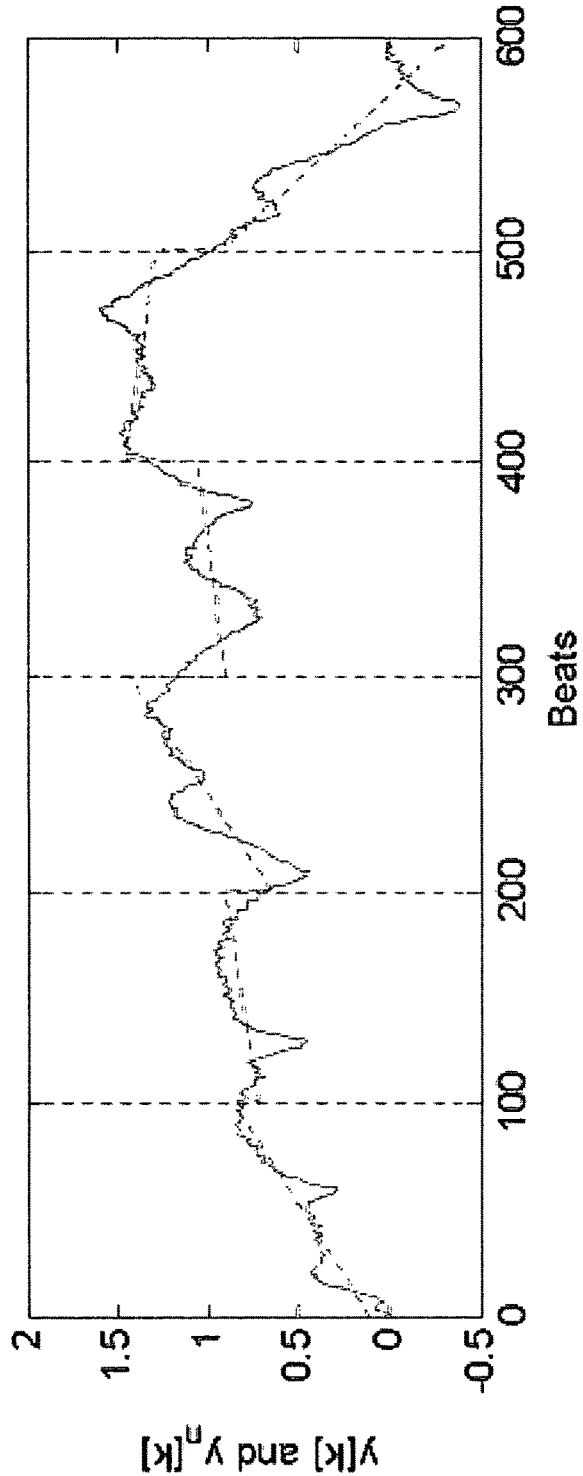
FIG. 7 is a graph illustrating an example of detrended fluctuation analysis.

(c) Detrended Fluctuation Analysis (DFA). DFA is a technique from statistical physics useful for determining long-term correlation in non-stationary time series. DFA was computed on ten-minute epochs of the RR interval, pulse amplitude and pulse arrival time, sliding at thirty-second intervals. For each epoch, the DFA process is:
  i. The time series (of length N) is first demeaned and integrated to get y[k].
  ii. It is then divided into segments each of size n (FIG. 7).

iii. It is then piece-wise detrended according to the segments (FIG. 7) to get y[k]-$y_n$[k].
iv. F is then computed as the root mean square of y[k]-$y_n$[k], i.e.

$$F[n] = \sqrt{\frac{1}{N}\sum_{k=1}^{N}(y[k]-y_n[k])^2}$$

v. The above is repeated for different values of n to obtain F[n].
vi. The log transform is then taken to produce the fluctuation function G[n], i.e. G[n]=$\log_{10}$(F[n]).

Another feature that can be obtained is the scaling exponent, which is the slope of the line obtained by regressing G[n] on $\log_{10}$n. In prior art, Penzel et al suggested the scaling exponents obtained from RR intervals are different between sleep stages. Here we found the values G[n] to be a better feature for identifying deep sleep.

(d) Respiratory rate variability. This is the difference between instantaneous respiratory frequency and a baseline respiratory frequency. Instantaneous respiratory frequency is calculated using two-minute, non-overlapping epochs of the PPG-derived respiration signal by taking the frequency with maximum spectral power between 0.15-0.4 Hz. Baseline respiratory frequency is calculated in the same way using ten-minute, non-overlapping epochs. This feature is useful for identifying deep sleep as respiratory frequency tend to be highly regular during these periods.

(e) Time and Frequency Analysis. This includes time and frequency domain descriptors of variability in the RR interval, pulse amplitude and pulse arrival time. Examples include standard deviation and spectral power in the low-frequency band.

(f) Multi-Scale Entropy (MSE). MSE is a statistical physics technique useful for revealing changing complexity across different scale factors in complex time series. MSE was computed on ten-minute epochs of the RR interval, pulse amplitude and pulse arrival time, sliding at thirty-second intervals. For each epoch, the MSE process is as follows:
i. The time series (of length N) is first linearly detrended to get x[k].
ii. For a particular scale factor τ, y is then computed by taking the running mean of τ consecutive, non-overlapping values of x[k], i.e.

$$y^{(\tau)}[p] = \frac{1}{\tau}\sum_{k=(p-1)\tau+1}^{p\tau} x[k] \text{ where } 1 \leq p \leq N/\tau.$$

iii. The above is repeated for different values of τ to obtain $y^{(\tau)}$[p].
iv. Sample entropy is then computed for each $y^{(\tau)}$[p]. For a given time series, its sample entropy is given by:

SE=ln(A/B)

where A is the total count of m-point matches, and B is the total count of m+1 point matches. A m-point match occurs when another set of m-points is within a range of ±r of it. For example, m can be 1 and r can be 15% of the standard deviation of the time series.

Figure 8:
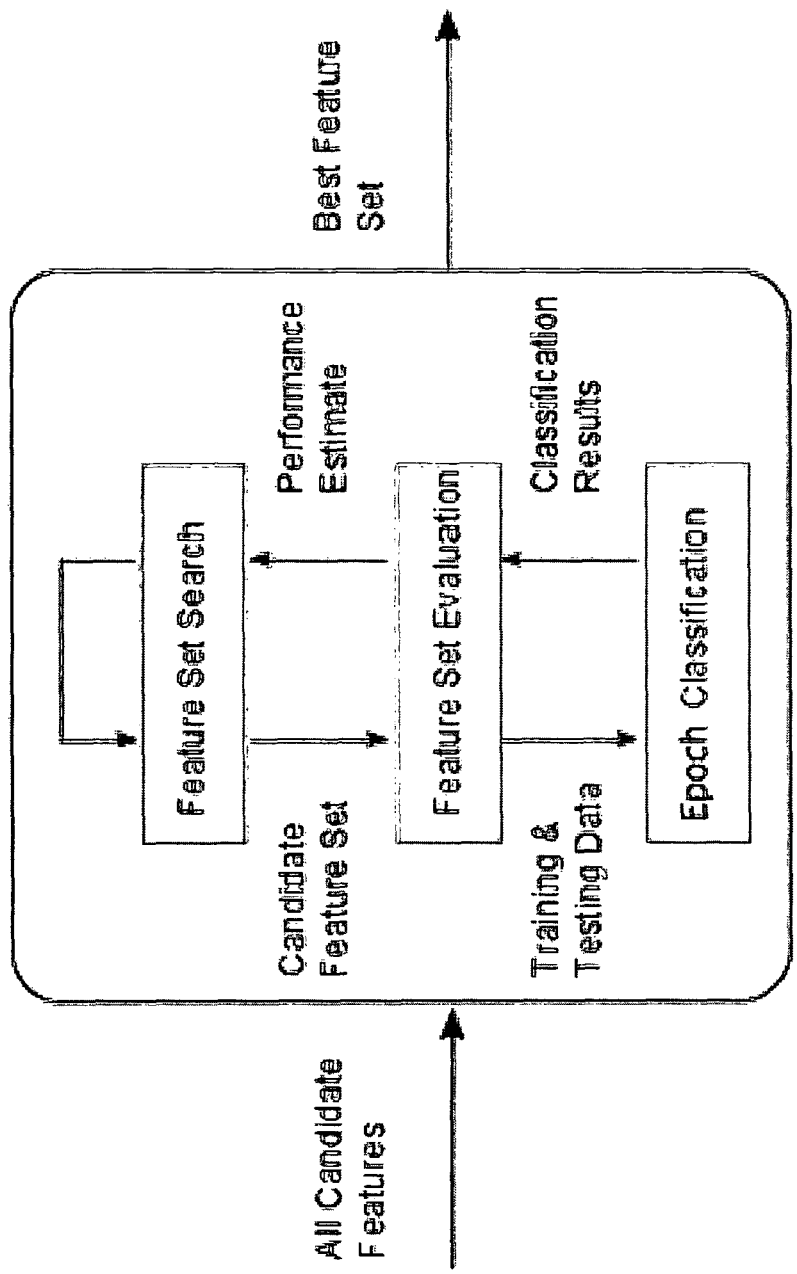
FIG. 8 illustrates a wrapper-based search process.

In the classification stage 16, sleep state estimates (wakefulness, REM, non-REM) are obtained as follows:
(a) Feature Selection. Preferably, the features described are calculated for the entire recording, with one feature vector (made up of all the features) describing each thirty-second epoch. A subset of the features can then selected using feature selection methods in conjunction of a training data set. The feature subset that optimises a certain performance measure, such as classification accuracy, is selected. For example, a wrapper-based search engine as depicted in FIG. 8 can be employed for this purpose. Briefly, this is an iterative procedure that takes in the entire feature set and outputs a subset of it that optimises a certain performance measure, such as classification accuracy. The modules of this engine are:
i. Feature Set Search. All possible feature subset combinations are systematically evaluated if technically feasible. Otherwise, a search algorithm such as best-first search is used to systematically evaluate feature subsets.
ii. Feature Set Evaluation. This module evaluates each feature subset generated by the Feature Set Search module, and returns its performance estimate. Evaluation can be performed by cross-validation methods such as leave one subject out cross validation, where for each subject, data from all other subjects are used for training, and data from that subject in question is used for testing.
iii. Epoch Classification. This module uses training data to train a classification model, such as a linear discriminant model, and uses the trained model to classify testing data. The module then returns the classification results.

The following table presents a list of example features that can be generated by the feature selection process, to be used subsequently for distinguishing sleep states.

| No. | Parameter | Feature |
| --- | --- | --- |
| 1 | PPG | PPG spectral spread |
| 2 | RR interval | DFA G[181] |
| 3 | PPG | Pulse amplitude |
| 4 | Pulse arrival time | Percentage of successive values differing by >50 ms |
| 5 | Pulse arrival time | Normalised low-frequency spectral power (0.04-0.15 cycles/interval) |
| 6 | Pulse amplitude | DFA scaling exponent |
| 7 | Pulse arrival time | MSE (scale: 8 beats) |
| 8 | PPG | Respiratory rate variability |

(b). Linear Discriminants. The selected feature subset is extracted to form consecutive feature vectors, each describing a thirty-second epoch. The features are then supplied to a linear discriminant classifier model, which produces probabilities of each epoch being associated with wakefulness, REM sleep or non-REM sleep.

(c) Post-processing. The probabilities are then smoothed to reduce epoch to epoch variability and then adjusted using heuristic rules based on normal sleep physiology in the population with suspected sleep apnoea. These adjustments include setting the probability for REM sleep to zero for the first 60 minutes of the recording, multiplying by a window that increases linearly from 0 to 1 from 60 to 100 minutes of the recording. Another adjustment is to set the probability for non-REM sleep to zero for the first ten minutes of the recording.

(d) Maximum A posteriori classification. The epochs are then classified into wakefulness, REM sleep or non-REM sleep epochs by assigning them to the class with the maximum adjusted probabilities.

(e) Heuristic correction. The classifications are then adjusted using heuristic rules, including reclassifying sections of non-REM sleep shorter than three minutes which are preceded and followed by REM sleep to REM sleep. Another adjustment is to reject short, isolated REM blocks of at most two-minute duration, and to reclassify these epochs to the class with next highest probability. Another adjustment is to reclassify as wake, short isolated sleep blocks of at most one-minute duration centred on a ten-minute block consisting entirely of wake.

Figure 3:
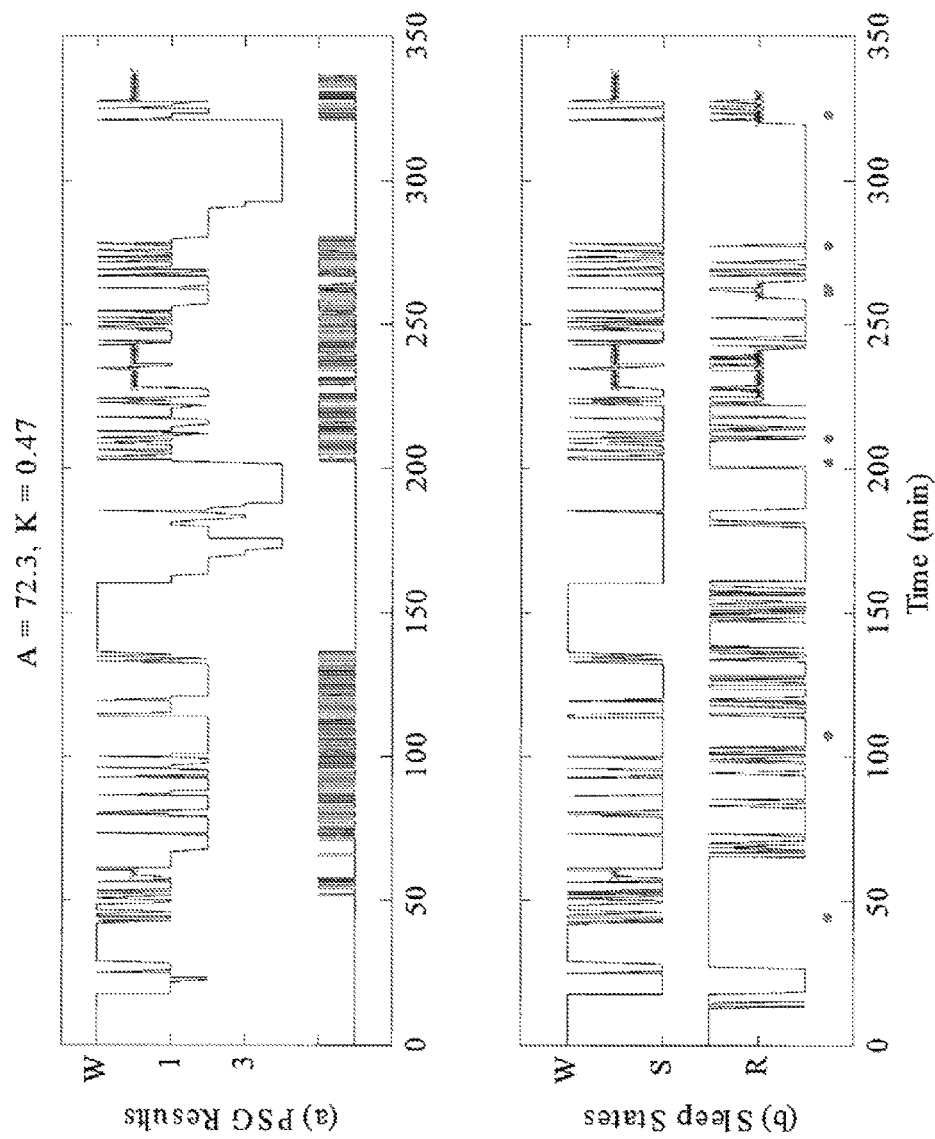
FIG. 3 is a diagram illustrating the output of the system of FIG. 1 for estimating sleep states.

FIG. 3 gives an example of the classification output by comparing it with the output obtained from standard in-laboratory procedures (polysomnography). (a) Top: Polysomnography-scored sleep stages, Bottom: Apnoea events (High=event). (b) Top: Polysomnography-scored sleep stages collapsed to Wake, REM and Sleep states, Bottom: Corresponding estimated sleep states (Dots indicate epochs that were heuristically corrected). Classification accuracy was 72.3%, and corresponding Cohen's kappa, which considers accuracy after discounting agreement by chance, was 0.47.

Figure 4:
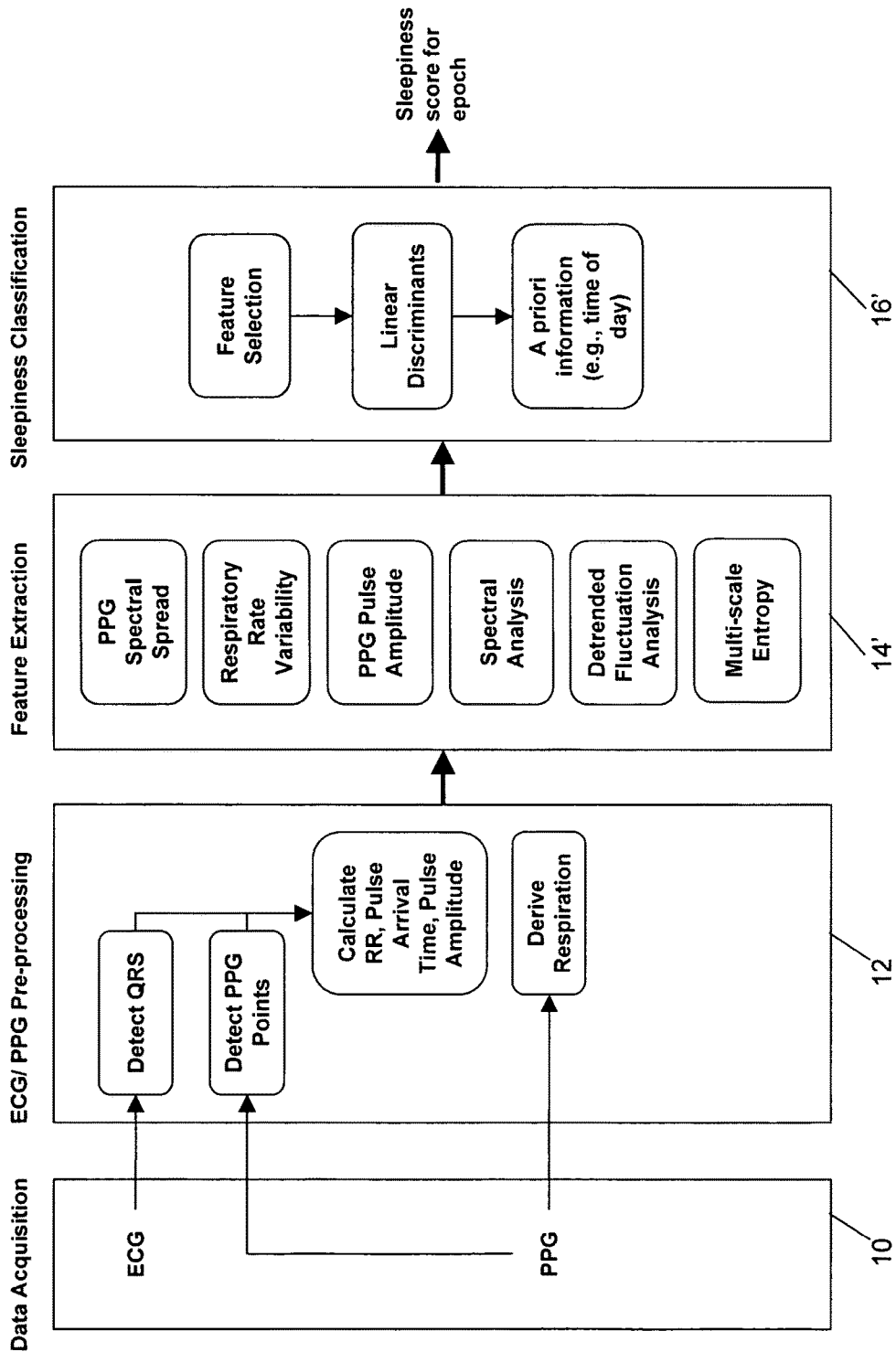
FIG. 4 is a block schematic diagram of a system for estimating sleepiness according to a second embodiment of the present invention.

FIG. 4 is a block schematic diagram of a system for estimating sleepiness according to a second embodiment of the present invention. The system comprises a data acquisition apparatus 10 and data processing stages 12, 14' and 16'. Apparatus 10 and stage 12 are the same as the corresponding components of the first embodiment.

In the feature extraction stage 14', the following features are derived from the ECG and PPG signals: PPG spectral spread, respiratory rate variability, PPG pulse amplitude, time and frequency analysis, detrended fluctuation analysis and multi-scale entropy. The features are calculated in the same way as described in relation to FIG. 1, except that in this embodiment these features are calculated on one-minute, non-overlapping epochs of data.

In the classification stage 16', a subset of features associated with each epoch is first selected using feature selection techniques. The process is conducted in the same way as described in relation to FIG. 1. This subset of features is then fed into a linear discriminant classification model, which is trained to distinguish between the alert and sleepy states. The classification model produces and outputs the probabilities of each epoch being associated with a sleepiness score. A priori information (such as time of day) may be used in calculating the discriminant values for the one minute epoch. Epochs of different length (e.g., from 10 seconds to hours) could also be used in assessing sleepiness.

Figure 5:
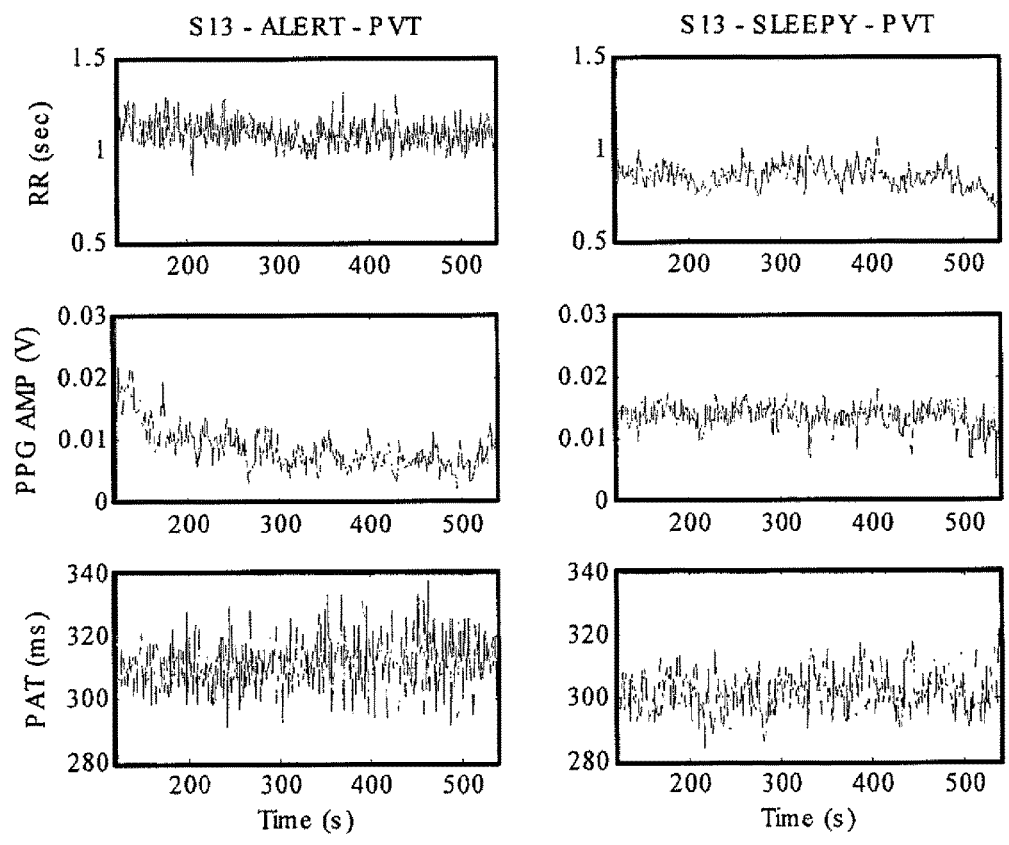
FIG. 5 is an example of the variation in features derived from RR interval, pulse arrival time, and pulse amplitude for an individual in an alert state (left hand column) and a sleepy state (right hand column).

FIG. 5 provides an example of how the features derived from RR interval, pulse arrival time, and pulse amplitude vary for an individual in an alert state (left hand column) and a sleepy state (right hand column). The general decrease in variability in the RR interval and pulse arrival time and the general increase in variability in pulse amplitude can be observed qualitatively. Differences in mean levels of heart rate and pulse amplitude can also be observed.

Figure 6:
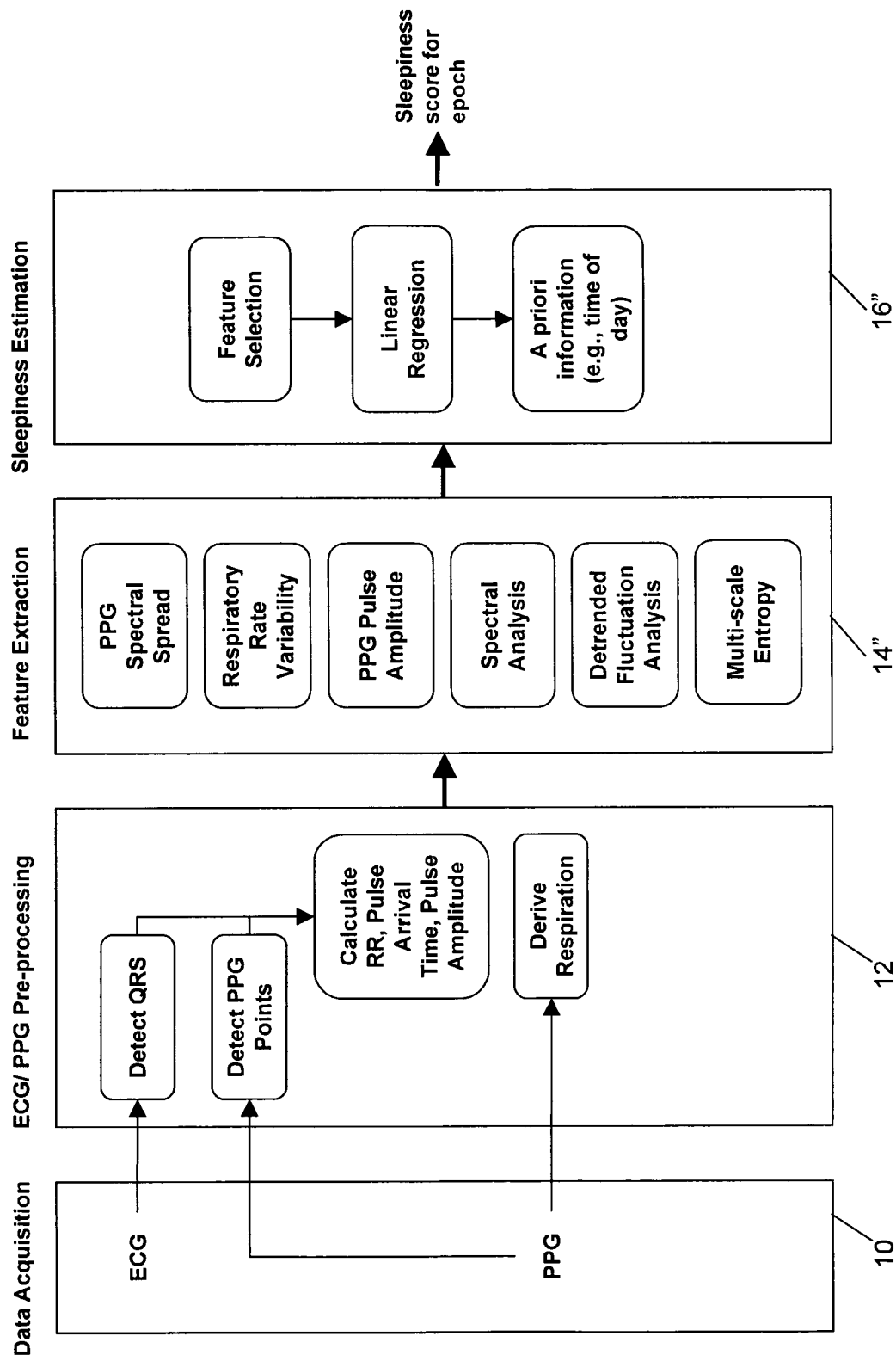
FIG. 6 is a block schematic diagram of a system for estimating sleepiness according to a third embodiment of the present invention.

FIG. 6 is a block schematic diagram of a system for estimating sleepiness according to a third embodiment of the present invention in which an objective estimate of sleepiness is obtained based on agreement with psychomotor vigilance test (PVT) scores. The system comprises a data acquisition apparatus 10 and data processing stages 12, 14" and 16". Apparatus 10 and stage 12 are the same as the corresponding components of the first embodiment.

In the feature extraction stage 14", the following features are derived from the ECG and PPG signals: PPG spectral spread, respiratory rate variability, PPG pulse amplitude, time and frequency analysis, detrended fluctuation analysis and multi-scale entropy. The features are calculated in the same way as described in relation to FIG. 1, except that in this embodiment these features are calculated on ten-minute, non-overlapping epochs of data.

In the sleepiness estimation stage 16", a subset of features associated with each epoch is first selected using feature selection techniques such as stepwise regression. Briefly, in stepwise regression, features are systematically evaluated in terms of a performance measure such as partial correlation with PVT scores, and features with statistically significant partial correlation with PVT scores are selected.

The following table presents a list of example features that can be generated by the feature selection process, to be used subsequently for estimating PVT scores.

| No | Parameter | Feature |
|---|---|---|
| 1 | RR Interval | Heart rate |
| 2 | RR Interval | Spectral power in low-frequency band (0.04-0.15 cycles/interval) |

The selected feature subset is then fed into a multiple linear regression model, which is trained to provide estimates of PVT scores based on a linear combination of the feature subset. The regression model can also use a priori information (such as time of day) in calculating the estimated PVT score for the ten minute epochs.

Experimental Results

Sleep State Monitoring 48 subjects representing the entire range of apnoea severity (Table I) were randomly recruited from patients referred to the Sleep Disorders Unit at St. Vincent's University Hospital, Ireland, for evaluation of suspected sleep apnoea.

TABLE I

Subject characteristics
(mean ± standard deviation, range)

| Male:Female | 42:6 |
|---|---|
| Age (years) | 49 ± 10 (28-73) |
| Body Mass Index (kg/m$^2$) | 31 ± 6 (21-49) |
| Apnea Hypopnea Index (hr$^{-1}$) | 25 ± 32 (0-171) |
| Epworth Sleepiness Scale | 11 ± 6 (0-23) |

All subjects underwent standard overnight diagnostic testing for sleep apnoea (polysomnography). ECG and PPG measurements were simultaneously taken using the system described above for sleep state monitoring. Post-polysomnography, experienced sleep technologists performed standard Rechtschaffen and Kales sleep-staging and scoring of respiratory events. Table II summarises the subjects' sleep stage characteristics.

TABLE II

Sleep stage characteristics obtained
from polysomnography

| Sleep State | Proportion of total time in bed (%) |
|---|---|
| Wake | 23 ± 14 (5-75) |
| REM | 14 ± 7 (0-29) |
| Non-REM | 62 ± 11 (21-79) |

The available records were sorted by the subjects' Apnoea-Hypopnea Index (obtained from polysomnography) and assigned alternately to either the training or validation set, yielding training and validation sets of 24 subjects each. This method for splitting the data was used to control for the possible influence of apnoea severity on sleep state estimation.

The system described above was trained using the training set and tested on the validation set. Table III summarises the training and validation classification performance. As shown, performances on the training and validation data set were in close agreement, indicating the robustness of the classifier. Overall, a classification accuracy of 73.5±7.7% (Cohen's kappa=0.49±0.12) was achieved. To separately quantify the performance contribution of the linear discriminant classifier model and the heuristic corrections, Table III also presents the results without heuristic corrections. As expected, the heuristic corrections were useful, but the bulk of performance was contributed by the classifier model.

TABLE III

Sleep state estimation performance

|  | Training Set | Validation Set |
| --- | --- | --- |
| With Heuristics Correction | | |
| Accuracy (%) | 72.8 ± 8.2 | 74.1 ± 7.3 |
| Kappa | 0.48 ± 0.13 | 0.50 ± 0.12 |
| Without Heuristics Correction | | |
| Accuracy (%) | 71.0 ± 8.7 | 72.4 ± 7.8 |
| Kappa | 0.45 ± 0.13 | 0.47 ± 0.12 |

There was also no significant correlation between classification performance and apnoea severity (r=−0.03, p=0.85), indicating that the performance of the classifier was limited by factors other than apnoea severity.

Table IV presents the overall confusion matrix combining results from the training and validation data set. Based on the confusion matrix, overall positive and negative predictive value pairs for each of the sleep states were as follows: Wake (64.1±12.9%, 88.7±9.8%), REM (50.8±23.6%, 94.5±4.5%) and Sleep (83.2±11.9%, 67.6±10.0%)

TABLE IV

Confusion matrix for sleep state estimation

| | | Reference (Polysomnography) | | | |
| --- | --- | --- | --- | --- | --- |
| | | Wake | REM | Sleep | Total |
| Estimate (Proposed System) | Wake | 5601 | 501 | 2813 | 8915 |
| | REM | 603 | 3644 | 2666 | 6913 |
| | Sleep | 2395 | 1220 | 18710 | 22325 |
| | Total | 8599 | 5365 | 24189 | 38153 |

Sleepiness Monitoring 15 young adults (5 M 10 F, aged 22±3 years, BMI 20.2±2.7 kg/m$^2$) with no known medical conditions were recruited. All subjects reported normal circadian and sleeping habits, and provided informed consent. Subjects identified a period of alertness and sleepiness each with respect to their normal routine and carried out the same experiment twice on the same day. All subjects chose the morning and afternoon, with a separation of 5.0±1.6 hours in between experiments, and had been awake for about 2.7 and 7.7 hours respectively when the experiments were conducted.

The experiment consists of two main tasks, performed consecutively in the sitting position. The first task was to watch a ten-minute video, and the second task was to perform a ten-minute Psychomotor Vigilance Test (PVT). Physiological measurements (including ECG, PPG, EEG, respiration and galvanic skin response) were taken throughout the video and PVT tasks.

The system described above for sleepiness monitoring was developed and tested on this set of data. Using a subset of features that are derived from the ECG and PPG, the classifier model was able to distinguish between alert and sleepy epochs recorded during both the video and PVT task with an accuracy of 72%±15% (Cohen's kappa=0.43±0.31). Performance was only slightly worse for classifying epochs from the PVT task (70%±21%, Cohen's kappa=0.40±0.42) compared to the video task (73±15%, Cohen's kappa=0.47±0.30), indicating that the classification algorithm is robust for classifying data recorded during different mental situations. Furthermore, using subject-specific classifiers, classification accuracies of 100% (Cohen's kappa=1) could be achieved for every subject. Certain features were consistently useful across subjects; however, to achieve full classification accuracy, different additional feature subsets were required for some subjects.

The invention is not limited to the embodiments described herein which may be modified or varied without departing from the scope of the invention.

The invention claimed is:

1. A method of monitoring sleep stages or level of sleepiness, the method comprising using one or more processors to:
    acquire and record data of a person's electrocardiogram (ECG) and photoplethysmogram (PPG), the data being acquired and recorded simultaneously,
    derive a plurality of parameters from both the recorded ECG and PPG data, wherein the plurality of parameters includes (1) at least one parameter derived from the ECG data independently of the PPG data, and (2) at least one parameter derived from the PPG data independently of the ECG data,
    extract features from the plurality of parameters, and
    provide an output indicative of a sleep stage or a quantitative level of sleepiness based upon an analysis of at least a subset of the extracted features from the derived plurality of parameters, wherein a trained statistical classifier in a processor of the one or more processors evaluates, on an epoch-by-epoch basis, the extracted features from both (1) the at least one parameter derived from the ECG data and (2) the at least one parameter derived from the PPG data, to generate the output indicative of the sleep stage or the quantitative level of sleepiness.

2. The method of claim 1, wherein the ECG and PPG data is acquired in an ambulatory manner.

3. The method of claim 2, wherein the ECG and PPG data is acquired using a combination of a Holter monitor and a pulse oximeter.

4. The method of claim 1, wherein the plurality of parameters include at least one of RR interval, pulse amplitude and respiratory rate.

5. The method of claim 4, wherein the plurality of parameters are analyzed by extracting the features, wherein the features are suitable for classifying sleep stages or quantitative level of sleepiness, and by feeding a subset of the features into a quantitative classifier to obtain an estimate of the sleep stage or quantitative level of sleepiness.

6. The method of claim 5, wherein the features include at least one of PPG spectral spread, PPG pulse amplitude, respiratory rate variability, detrended fluctuation analysis, time and frequency analysis and multi-scale entropy.

7. The method of claim 5, wherein the output is used to determine sleep stages comprising at least one of wakefulness, rapid-eye-movement sleep, and non-rapid-eye-movement sleep.

8. The method of claim 5, comprising assigning sleep stages or quantitative levels of sleepiness to specific epochs of time of greater than 10 seconds in duration.

9. The method of claim 8, comprising classifying a single epoch according to a classification of surrounding epochs.

10. The method of claim 5, further comprising estimating the output of a psychomotor vigilance test during wakefulness using the output of the quantitative classifier.

11. The method of claim 1, wherein the one or more processors derive an additional parameter from both the recorded ECG data and the recorded PPG data, and wherein the output indicative of a sleep stage or a quantitative level of sleepiness is based upon an analysis of parameters that includes the additional parameter.

12. The method of claim 11, wherein the additional parameter derived from both the recorded PPG data and the recorded ECG data is pulse arrival time.

13. The method of claim 1 wherein the subset of the extracted features from the plurality of parameters includes a feature derived by detrended fluctuation analysis.

14. The method of claim 1 wherein the subset of the extracted features from the plurality of parameters includes a feature derived by multi-scale entropy analysis.

15. The method of claim 1 wherein the trained statistical classifier evaluates a PPG spectral spread feature to generate the output indicative of the sleep stage or the quantitative level of sleepiness.

16. The method of claim 1 wherein the trained statistical classifier evaluates the extracted features from (1) the at least one parameter derived from the ECG data and (2) the at least one parameter derived from the PPG data, to generate the output indicative of the quantitative level of sleepiness.

17. The method of claim 1 wherein the trained statistical classifier evaluates the extracted features from (1) the at least one parameter derived from the ECG data and (2) the at least one parameter derived from the PPG data, to generate the output indicative of the sleep stage.

18. A system for monitoring sleep stage or level of sleepiness, the system comprising:
a sensing apparatus configured to simultaneously acquire electrocardiogram (ECG) and photoplethysmogram (PPG) data from a monitored subject;
a computer executable memory configured to record the acquired ECG and PPG data, and to store computer executable instructions; and
a processor configured to execute the computer executable instructions to derive a plurality of parameters from both the recorded ECG and PPG data, to extract features from the plurality of parameters, and to provide an output indicative of a sleep stage or a quantitative level of sleepiness based upon an analysis of at least a subset of the extracted features from the plurality of parameters, wherein the plurality of parameters includes (1) at least one parameter derived from the ECG data independently of the PPG data, and (2) at least one parameter derived from the PPG data independently of the ECG data, wherein the processor is configured with a trained statistical classifier that evaluates, on an epoch-by-epoch basis, the extracted features from both (1) the at least one parameter derived from the ECG data and (2) the at least one parameter derived from the PPG data, to generate the output indicative of the sleep stage or the quantitative level of sleepiness.

19. The system of claim 18, wherein the sensing apparatus is wearable in ambulatory manner.

20. The system of claim 19, wherein the sensing apparatus comprises a combination of a Holter monitor and a pulse oximeter.

21. The system of claim 18, wherein the processor is configured to derive an additional parameter from both the recorded ECG data and the recorded PPG data, and provide an output indicative of quantitative level of sleepiness or sleep stage based upon an analysis of parameters that includes the additional parameter.

22. The system of claim 21, wherein the additional parameter derived from both the recorded PPG data and the recorded ECG data is pulse arrival time.

23. The system of claim 18 wherein the subset of the extracted features from the plurality of parameters includes a feature derived by detrended fluctuation analysis.

24. The system of claim 18 wherein the subset of the extracted features from the plurality of parameters includes a feature derived by multi-scale entropy analysis.

25. The system of claim 18 wherein the trained statistical classifier is configured to evaluate a PPG spectral spread feature to generate the output indicative of the sleep stage or the quantitative level of sleepiness.

26. The system of claim 18 wherein the trained statistical classifier is configured to evaluate the extracted features from (1) the at least one parameter derived from the ECG data and (2) the at least one parameter derived from the PPG data, to generate the output indicative of the quantitative level of sleepiness.

27. The system of claim 18 wherein the trained statistical classifier is configured to evaluate the extracted features from (1) the at least one parameter derived from the ECG data and (2) the at least one parameter derived from the PPG data, to generate the output indicative of the sleep stage.

* * * * *